(12) United States Patent
Burke et al.

(10) Patent No.: US 11,273,068 B2
(45) Date of Patent: *Mar. 15, 2022

(54) BRACES HAVING INELASTIC AND ELASTIC MATERIALS

(71) Applicant: Fiji Manufacturing, LLC, Irvine, CA (US)

(72) Inventors: Steven Burke, Huntington Beach, CA (US); Jozsef Horvath, Fullerton, CA (US); Erik Zimmer, Oceanside, CA (US)

(73) Assignee: Aspen Medical Partners, LLC, Irvine, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 16/406,367

(22) Filed: May 8, 2019

(65) Prior Publication Data

US 2019/0262163 A1    Aug. 29, 2019

Related U.S. Application Data

(63) Continuation of application No. 15/516,860, filed as application No. PCT/US2016/037850 on Jun. 16, 2016, now Pat. No. 10,299,955.

(60) Provisional application No. 62/182,357, filed on Jun. 19, 2015.

(51) Int. Cl.
| | |
|---|---|
| *A61F 5/03* | (2006.01) |
| *A61F 5/02* | (2006.01) |
| *A61F 13/14* | (2006.01) |
| *A61F 13/00* | (2006.01) |

(52) U.S. Cl.
CPC ........ *A61F 5/028* (2013.01); *A61F 13/00038* (2013.01); *A61F 13/14* (2013.01); *A61F 13/148* (2013.01)

(58) Field of Classification Search
CPC ............ A61F 2013/00038; A61F 13/14; A61F 13/148; A61F 5/028; A61F 5/026; A41C 1/02; A41C 1/04; A41B 2300/22; A41B 2400/38
See application file for complete search history.

(56) References Cited

U.S. PATENT DOCUMENTS

| | | |
|---|---|---|
| 2,289,302 A | 7/1942 | Bradshaw |
| 3,783,879 A | 1/1974 | Stalder |
| 4,825,856 A | 5/1989 | Nelson |

(Continued)

FOREIGN PATENT DOCUMENTS

WO    2014038213    3/2014

OTHER PUBLICATIONS

Bauerfeind; SacroLoc. "Stabilizing orthosis for relief of the pelvis." www.bauerfeindusa.com. pp. 1-2.

(Continued)

*Primary Examiner* — Camtu T Nguyen
(74) *Attorney, Agent, or Firm* — Fish IP Law LLP (57) ABSTRACT

Lower back braces and materials for braces having an elastic base and inelastic strands or tightening mechanism(s) are provided. An elastic base material could be made effectively inelastic by tightening an inelastic cord that extends across the elastic base material. Additionally or alternatively, an elastic base material could include one or more inelastic strands that define one or more inelastic compression zones in an otherwise elastic base.

7 Claims, 8 Drawing Sheets

(56) References Cited

U.S. PATENT DOCUMENTS

| | | | |
|---|---|---|---|
| 5,820,575 | A | 10/1998 | Cabrera |
| 5,833,638 | A | 11/1998 | Nelson |
| 8,409,122 | B2 | 4/2013 | Cropper |
| 8,696,610 | B2 | 4/2014 | Solomon |
| 9,364,365 | B2 | 6/2016 | Omarsson |
| 9,554,935 | B2 | 1/2017 | Ingimundartson |
| 10,299,955 | B2* | 5/2019 | Burke ............... A61F 13/00038 |
| 2009/0306570 | A1 | 12/2009 | Bauerfeind |
| 2011/0213284 | A1 | 9/2011 | Garth |
| 2012/0078156 | A1* | 3/2012 | Platz ....................... A61F 13/08 |
| | | | 602/76 |
| 2013/0160328 | A1 | 6/2013 | Hatfield |
| 2014/0221893 | A1 | 8/2014 | Modglin |
| 2016/0206495 | A1* | 7/2016 | Pongratz ............... A61F 13/143 |

OTHER PUBLICATIONS

Cybertech Medical; Cybertech Pathway LS. www.cybertechmedical. com. pp. 1.
DJO Global; Donjoy Lumboforce. pp. 1-9.
Sporlaastic; Vertebradyn-Strong. www.sporlastic.de/de/main/platinum/074525.html. pp. 1.
Sporlaastic; Vertebradyn-Vario. pp. 1.

\* cited by examiner

BRACES HAVING INELASTIC AND ELASTIC MATERIALS

This application is a continuation of U.S. patent application Ser. No. 15/516,860 which is a National Stage of International Application number PCT/US16/37850, filed Jun. 16, 2016, which claims priority to U.S. Provisional Application Ser. No. 62/182,357, filed Jun. 19, 2015. This and all other extrinsic materials identified herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is inelastic and elastic materials, and elastic braces having inelastic zones of compression.

BACKGROUND

The background description includes information that can be useful in understanding the present invention. It is not an admission that any of the information provided herein is prior art or relevant to the presently claimed invention, or that any publication specifically or implicitly referenced is prior art.

Some flexible back support braces that users could comfortably wear for everyday general uses are known. However, such braces are largely ineffective in relieving lower back pain as they generally do not improve trunk stability to the extent inelastic braces do. Unfortunately, inelastic braces (e.g., braces having rigid edges that dig into the wearer's body or bulky, rigid plastic components) can be very restrictive for wearers, especially for those that require relief when working, exercising or engaging in other physical activities where mobility is beneficial. For this and various other reasons, users of elastic braces have found it difficult to transition to the more supportive inelastic braces.

While some efforts have been made to produce a brace that provides benefits of both flexible and inelastic braces, such efforts appear to focus primarily or solely on the breathability of base materials rather than on any of the other benefits of flexible or elastic base materials. Thus, these previous efforts fail to provide many of the desired benefits of flexible and inelastic braces.

For example, US 2009/0306570 to Bauerfeind teaches a tubular compression bandage that is inelastic laterally to the longitudinal direction and elastic in the longitudinal direction. More specifically, Bauerfeind's bandage is described as being custom made based on measurements of a user's leg. The bandage "fits snugly on a limb over the entirely length of the bandage," and "does not form any particularly tightly confined sites of constrictions."

As another example, Bauerfeind's SacroLoc® lower back brace includes segments that use a combination of elastic and non-elastic knit such that the brace can be stretched in the up-down direction, but appears to be inelastic in the right-left along the entire height of the segments. Because Bauerfeind's bandages and braces appear to be designed to be inelastic in the right-left direction over the entire height of the bandage or brace segments (e.g., to provide an even pressure), they largely eliminate the benefits of an elastic brace.

Thus, there is still a need in the art for improved braces and other wearable objects that incorporate various benefits of inelastic braces and elastic braces.

SUMMARY

The inventive subject matter provides a material having (1) an elastic base, and (2) one or more inelastic strands that are incorporated into the base to create or define one or more zones (areas) of inelasticity or compression, and methods of manufacturing the same. The term "elastic" should be interpreted broadly to include any object that is capable of repeatedly stretching to at least 110% of its original length and returning to its original shape in at least one direction. For example, an elastic base could include a knit, woven, braided, non-woven or other base material that is capable of repeatedly stretching to at least 120% of its original length and returning to its original shape in at least two directions.

The elastic base of an object, for example a brace, could be cut from an existing piece of material, could comprise a non-cut material (i.e., a piece of material that was knit, woven or braded specifically to form the base of the object), or a combination of both. It is contemplated that an elastic base can comprise one, two, or even more pieces of materials that are combined to form a single, integral, segmented piece.

The inelastic strand(s) are preferably incorporated into the base in a direction of the base's elasticity, and can be incorporated during the knitting or weaving process of the elastic base, or sewn on or threaded through the elastic base once completed. For example, where a base has a vertical height and a horizontal length, and is capable of stretching horizontally, the inelastic strand(s) can be incorporated horizontally (i.e., along a portion or all of the length of the base). The base can include inelastic strands at different heights of the base to thereby reduce its elasticity at selected portions of the base. Where the inelastic strands are incorporated during the knitting or weaving process of the elastic brace, it is contemplated that the inelastic strands may in some embodiments not be separable from the elastic base without damaging the elastic base.

One should appreciate that the disclosed subject matter provides many advantageous technical effects including the flexibility and comfort of an inelastic brace while also providing improved stability to targeted portions of the body. It should also be appreciated that the systems and methods of the inventive subject matter described herein do not require, or even benefit from numerous bulky rigid components found in many prior art devices, and thus can unobtrusively be worn under clothing.

In some aspects, the elastic base can be elastic in first and second orthogonal directions. Additionally or alternatively, the elastic base can have the same elasticities in first and second orthogonal directions. One or more inelastic strands can be incorporated into the elastic base in one of the elastic directions to reduce or eliminate the elasticity in that elastic direction at a selected inelastic zone where the inelastic strand(s) is located. The inelastic zone can have a height that is less than 50%, less than 30%, less than 25%, less than 20%, less than 15%, less than 10% or even less than 5% of the height of the elastic base. The inelastic zone can have a length that is at least 10%, at least 20%, at least 30%, at least 40%, or even 50% or more of the length of the elastic base. In some embodiments, multiple inelastic zones can be provided.

Viewed from another perspective, the material (the elastic base with inelastic strands incorporated therein) could have a different elasticity than the elastic base, at least in a first direction in which an inelastic strand is incorporated, or a direction substantially parallel to the direction in which the inelastic strand is incorporated. In some preferred embodiments, the material will have varying elasticities along its height or width since the inelastic strands are selectively incorporated into only portions of the elastic base.

The one or more inelastic strands incorporated through the elastic base can be incorporated to have various shapes. For example, one or more inelastic strands can be incorporated as a straight line, one or more inelastic strands can be incorporated as a slightly curved line (e.g., a curve having a vertical height that is less than 10% of its horizontal length when positioned horizontally lengthwise), and one or more inelastic strands can be incorporated as zigzagging lines having the same or different zigzag shapes.

It should be appreciated that the size, length and specific shape of the inelastic strands as incorporated into the elastic base can affect the level of inelasticity of each of the inelastic zones. Viewed from another perspective, it is contemplated that the material described above can have an elasticity in the first direction along one or more zones that is between 10-100% less than, between 25-75% less than, between 25-50% less than, between 50-100% less than, or between 75-100% less than an elasticity in the second direction.

The inelastic strand(s) can be incorporated into the elastic base to effectively reduce the elasticity of the elastic base in the first direction by at least 10%, by at least 25%, by at least 50%, by at least 75%, or by at least 90% or even more (along the inelastic zone(s)). Viewed from another perspective, the material can have an elasticity in the first direction along one or more zones that is at least 10%, at least 25%, at least 50%, at least 75%, or even at least 95% less than the elasticity of the elastic base itself in the first direction. Where an inelastic strand is incorporated into a base material in a straight line, the material could be completely inelastic in the direction the strand is incorporated (along the length of the inelastic zone).

The term "the same" is not intended to be overly limiting and should be interpreted as including things that are exactly the same, and things that are substantially the same (within 10%). For example, the term substantially the same elasticity can include first and second elasticities that are identical, within 1%, within 5%, within 8%, or within 10% of one another. The term "orthogonal" should similarly be interpreted broadly as including angles that are exactly orthogonal, and angles that are substantially orthogonal to one another (within 10 degrees of orthogonal, inclusive).

The term "zigzag" or "zigzagging" includes any line or shape that alternately moves right and left, or up and down at least five (5) times. The alternating points of a zigzag can be pointy (e.g., "w" shaped zigzags), curved (e.g., s shaped zigzags), or even flat (e.g., ] and [ shaped zigzags) or irregularly shaped.

The inventive subject matter also provides lower back braces and methods of manufacturing the same, for example, using a material as described above. Contemplated lower back braces can comprise a continuous or segmented belt having a mid-portion disposed between two lateral portions. One, two or all of the portions can have a material comprising at least one of (1) an elastic base that is elastic in one or more directions, (2) one or more inelastic strands incorporated into the elastic base material and modifying an elasticity of the elastic base in at least one elastic direction along zones created by the inelastic strand(s), and (3) an overall elasticity (including the elastic base and inelastic strand(s)) in a first direction and along zones created by the inelastic strand(s) that is different from an elasticity of the elastic base without the inelastic strands.

Where one or more portions include a material made from a knitted elastic base, the knitted base can include one or more elastic strands, one or more inelastic strands, or a combination of both. Where one or more portions include a material made from a woven elastic base, the woven base can include warp and weft strands, which can comprise one or more elastic strands, one or more inelastic strands, or a combination of both.

The one or more inelastic strands that are sewn, threaded through or otherwise incorporated into the elastic base (during the process of knitting or weaving the elastic base, or after the elastic base has been knit or woven) can define one or more inelastic zones where greater pressure can be applied to targeted portions of the wearer's body by the base when the brace is worn.

The two lateral portions can each comprise an elastic base having the same or different elasticities in first and second orthogonal directions. For example, the elastic base could have no elasticity in a first direction (e.g., a vertical, up-down direction when the brace is worn), but have an elasticity in a second direction (e.g., a horizontal, right-left direction when the brace is worn) that allows the base to stretch to at least 110%, at least 120%, at least 130%, at least 140%, at least 150% or even more of its original length while subsequently returning to its original shape. Additionally or alternatively, the elastic base could have an elasticity in the first direction that allows the base to be stretched to at least 110%, at least 120%, at least 130%, at least 140%, or at least 150%, and have an elasticity in the second direction that allows the base to stretch to a maximum of between 105-150%, between 110-150%, between 125-150%, between 110-135%, or between 110-125% of its original length while subsequently returning to its original shape.

One or more inelastic strands could be incorporated into the base, each having a diameter of less than 1 cm (0.3937 inch), more preferably less than 0.5 cm (0.1969 inch). The inelastic strands could define one or more inelastic zones where increased compression or trunk stability could be provided, and each zone could comprise 1, 2, 3, 4, or even 5 or more inelastic strands. In some preferred embodiments, each inelastic zone has a height of less than 2 inches (5.08 cm) (e.g., less than 1 inch (2.54 cm), less than 0.5 inch (1.27 cm)), a length of at least 1 inch (2.54 cm) (e.g., at least 2, at least 3, at least 4, at least 5, at least 6, at least 7, or even 8 or more inches), and is separated from a neighboring inelastic zone by at least 1 cm (0.3937 inch) (e.g., at least 1 inch (2.54 cm), at least 2 inches (5.08 cm)). In some preferred embodiments, each inelastic zone comprises a set of inelastic strands (e.g., 2, 3, 4, 5 or even more inelastic strands) that extend parallel to one another, and are spaced apart by less than 10 mm (0.3937 inch), more preferably less than 5 mm (0.1969 inch).

In some embodiments, the lateral portion can be viewed as having several sections that are positioned in series vertically when the brace is worn (even where the lateral portion comprises a single, continuous piece). One or more of these sections can have an elasticity that is reduced relative to the elastic base by the incorporation of one or more inelastic strands, while other sections retain full elasticity. The sections that include the inelastic strands can have an elasticity in a horizontal direction that is reduced by between 10-100%, by between 20-100%, by between 50-100%, by between 75-100%, by between 90-100%, or by between 95-100% compared to the sections that do not include inelastic strands.

Viewed from another perspective, the lateral portions (or any other portion of the belt) can have horizontal, side-to-side elasticities that vary along the vertical height. For example, the lateral portion could have an elasticity horizontally that is reduced by at least 50%, at least 70%, at least 80% at least 90% or even 95-100% along portions where inelastic strands are incorporated, but have an elasticity horizontally that is not reduced along portions lacking an inelastic strand. While a neighboring inelastic strand of a section could make it more difficult to stretch sections of the lateral portion that lack any inelastic strands, it should be appreciated that the actual elasticity of the sections lacking the inelastic strands is not affected.

In some embodiments, the mid-portion of the brace can comprise an elastic material and be coupled with a tightening mechanism that includes at least one inelastic cord that extends across a length of the mid-portion. The mid-portion can lack an inelastic strand that defines an inelastic zone, and a user could tighten or loosen the tightening mechanism to prevent or allow the mid-portion to stretch when the brace is worn.

As described above, it is contemplated that the mid-portion and two lateral portions could have an elastic base that is non-cut, and at least one of knit, woven and braided as a single, continuous piece. Additionally or alternatively, the mid-portion and two lateral portions could comprise an elastic base that is a single, continuous cut piece of material. Additionally or alternatively, each portion's base (or at least two of the portions' bases) could comprise distinct pieces of materials that are removably or permanently attached to one another to form a single, segmented piece. Additionally or alternatively, each portion's base (or at least two of the portions' bases) could comprise distinct pieces of materials that are indirectly coupled to one another (e.g., via cords, panels, connectors, or other pieces of material).

In some contemplated embodiments, the entire top edge or the entire bottom edge of a brace or portions thereof could be made to lack inelastic strands and materials such that they maintain a greater elasticity than portions including inelastic strands. Alternatively, the top or bottom edges could include inelastic strand(s) in a zigzagged configuration to allow for greater elasticity than the central portion. Alternatively or additionally, the top or bottom edges could include an elastic strand that is less elastic than the base material, but more elastic than the inelastic strands. Viewed from another perspective, the brace belt will preferably have a greater elasticity along the top and bottom edges compared to the mid-section of the brace when worn.

It is advantageous to configure the brace belt such that it is sufficiently elastic in the horizontal direction along top and bottom edges to conform to the curvatures or a wearer without pinching or otherwise causing discomfort. Each of the top and bottom edges could comprise at least 2%, more preferably at least 5%, and even more preferably at least 10% of the height of the belt. Viewed from another perspective, the top and bottom 5-15% of the belt could be horizontally elastic to conform to the ribcage and hips of a wearer, while the mid-70-90% could comprise a plurality of inelastic zones dispersed therein. Additionally or alternatively, the top and bottom edges can have an elasticity that is at least 70%, at least 80%, at least 90% or even at least 100% of the elasticity of the elastic base material.

Such a distribution of elastic and inelastic zones along the brace belt can advantageously provide a wearer with targeted areas of compression to stabilize the wearer's trunk while maintaining the comfort of a flexible belt where inelasticity is not as needed or beneficial.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Braces and materials for braces and other wearable items that include inelastic elements incorporated into or over elastic bases are provided. Such braces can advantageously give users the support of inelastic braces while also providing the comfort and flexibility of elastic braces.

Materials of the inventive subject matter can include (1) an elastic base, and (2) one or more inelastic strands incorporated into the elastic base that create or define a zone (area) of inelasticity. The elastic base can in some embodiments be made primarily or entirely of elastic strands and can have an elasticity in a first direction that is the same as an elasticity in a second direction orthogonal to the first direction.

A method of producing such materials can include knitting, weaving, braiding, or cutting an elastic material to form base that is elastic in at least a first direction, and incorporating a first inelastic strand across a first portion of the base, and along the first direction, to create a first zone of inelasticity. Some methods can include the additional step of incorporating a second inelastic strand across a second portion of the elastic base in the first direction (or a direction substantially parallel to the first direction) to create a second zone of inelasticity. Each of the first and second strands could be incorporated to have any of the characteristics described below.

The inelastic strand(s) incorporated into the elastic base can advantageously be, among other things, a yarn, thread, fiber, plastic, wire, a hook or loop material, or other inelastic piece of material having a width that is less than 2 inches (5.08 cm), more preferably less than 1 inch (2.54 cm), or even less than 1 cm (0.3937 inch), to provide a thin inelastic zone extending across a length of the material. However, inelastic strands of any suitable thickness are contemplated, especially those having a thickness that is less than $1/10^{th}$ or less than $1/20^{th}$ the height of the elastic base it is incorporated into. The inelastic strands could create inelastic zones of any suitable thickness, especially those having a thickness that is less than $1/5^{th}$ or less than $1/10^{th}$ the height of the elastic base it is incorporated into.

The material, comprising the inelastic strand(s) incorporated into the elastic base, can have an elasticity in the first direction (e.g., horizontal) that is at least 50% less than (more preferably at least 75% less than, or even at least 90% less than) an elasticity in the second, orthogonal direction (e.g., vertical). Additionally or alternatively, a portion of the material that includes one or more inelastic strands could have an elasticity in the first direction that is at least 50% less than (e.g., at least 75% less than, at least 90% less than) the elasticity of the same portion of the elastic base alone. The reduction in elasticity in the horizontal direction could be with respect to the entire vertical height of the material, or only portions thereof. For example, the reduction in elasticity in the horizontal direction could be limited to the areas along the vertical height of the material where the inelastic strands are incorporated. Viewed from another perspective, it is contemplated that horizontal sections of the material where inelastic strands are not incorporated can retain more elasticity than horizontal portions of the material where the inelastic strands are incorporated.

The material can be used to make portions of a brace, for example a belt of a lower back brace. Although the discussion herein generally relates to lower back braces incorporating the material of the inventive subject matter, a person skilled in the art would be able to use the teachings herein to make and use various other braces. Contemplated braces include, among other things, ankle braces, knee braces, back braces, neck braces, wrist braces, and any other suitable medical, sports or other braces in which specific zones of inelasticity are desirable. Where the brace incorporates a material having an elastic base (cut or non-cut), it is contemplated that the elastic base can be flat knit (e.g., for lower back braces), circular knit (e.g., for ankle, knee and wrist braces), woven, braided, or made in any other suitable manner. The elastic base could comprise one or more different strands and strand types, including for example, elastic strands (e.g., spandex strands or fibers) and inelastic strands.

Some contemplated back braces incorporating the material described herein could include a belt having a mid-portion disposed between right and left lateral portions. The entire belt could comprise a continuous elastic base, and an inelastic strand could be used to create permanent areas or zones of inelasticity throughout the elastic base. Alternatively or additionally, the belt could be segmented and made from one or more separate pieces of cut or non-cut material(s).

The top and bottom edges of some or all portions of the lower back brace can optionally be free of any inelastic strands, which would allow for the brace to conform tightly to a wearer's waist and lower back, while maintaining elasticity near the ribcage and hip regions for flexibility and comfort. Where an inelastic strand is included on a top or bottom edge (for example, for stitching), the inelastic strand can be incorporated in a zigzagging pattern such that the top or bottom edge retains some or all of the elasticity of the elastic base.

It should be appreciated that any suitable number of inelastic zones could be included into a brace of the inventive subject matter, and the inelastic zones could have any suitable length, width and curvature. Alternatively or additionally, one or more of the brace portions can include elastic strands that are less elastic than the base material and create or define one or more elastic areas/zones that can provide greater compression than other portions of the brace.

When a brace having inelastic zones is worn by the wearer, the inelastic zones can remain inelastic in a side-to-side (or other) direction and therefore tightly compressed against the wearer. Since the top and bottom edges of the belt can remain elastic in a side-to-side direction, pinching of the wearer's body along the rib and hip areas can be avoided, even for wearers of different sizes and shapes.

Figure 1A:
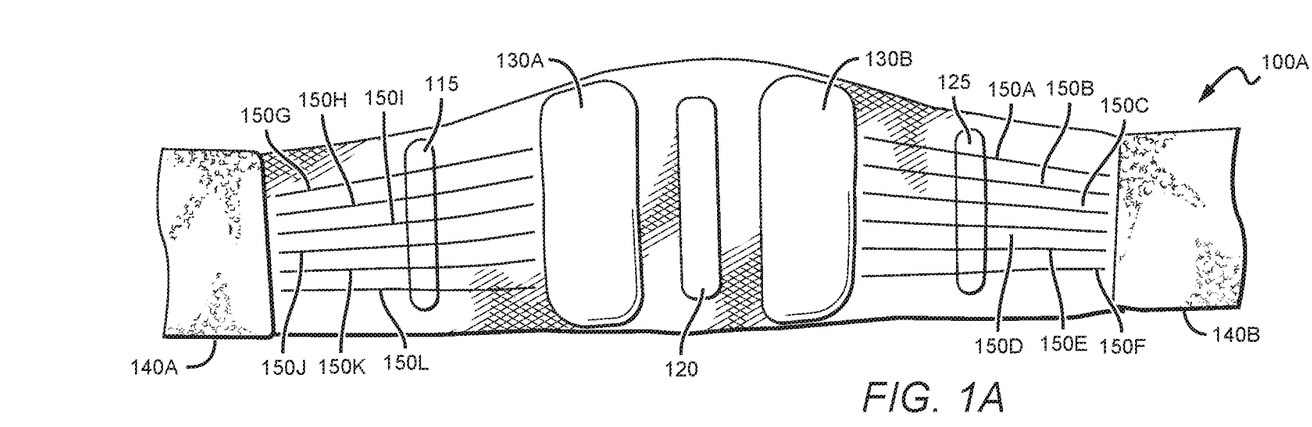
FIG. 1A illustrates an inner surface of a brace of the inventive subject matter.
Figure 1B:
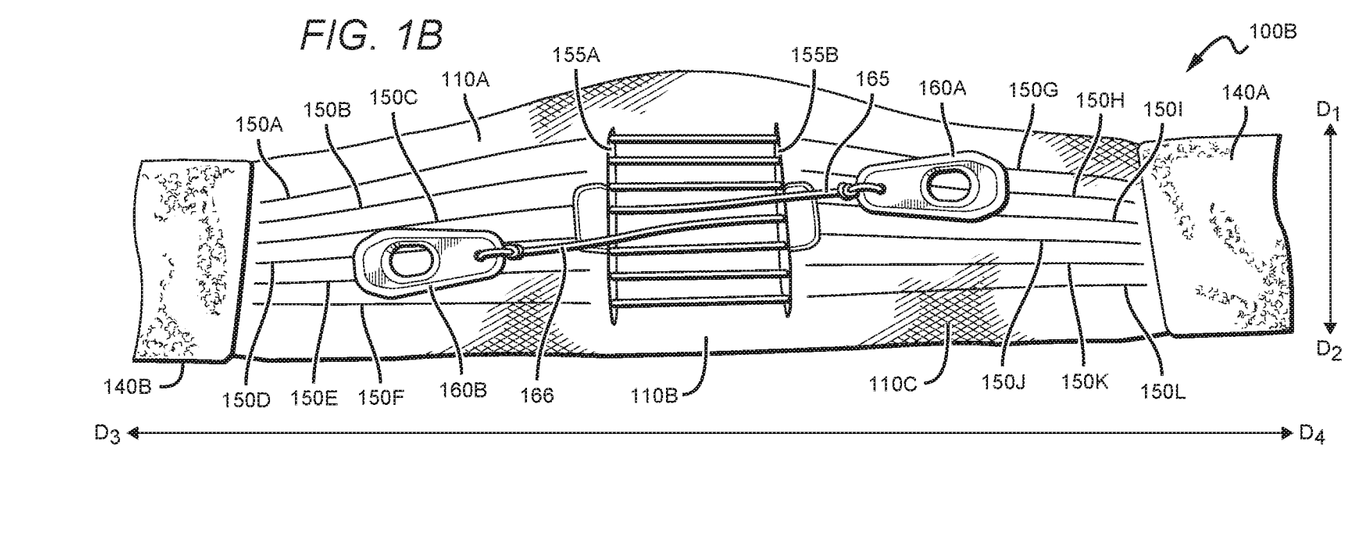
FIG. 1B illustrates an outer surface of the brace of FIG. 1A.

An exemplary lower back brace according to the inventive subject matter is illustrated in FIGS. 1A-1D. FIG. 1A illustrates the inner side 100A of the brace (i.e., the side facing the wearer when the brace is worn), and FIG. 1B illustrates the outer side 100B of the brace (i.e., the side facing the environment around the wearer when the brace is worn).

The brace of FIGS. 1A-1D includes a mid-portion 110B disposed between left lateral portion 110A and right lateral portion 110C. Portions 110A, 110B and 110C are shown as including a continuous base that extends across the entire length of portions 110A, 110B and 110C. The elastic base can in some embodiments have an elasticity in direction D1-D2 that is the same as an elasticity in direction D3-D4 (or any other direction). For example, the elastic base can be configured to (a) stretch to a maximum of between 110-120% of its original length in the horizontal D3-D4 direction and resume its original length, and (b) stretch to a maximum of between 110-120% of its original length in the vertical D1-D2 direction and resume its original length. In other embodiments, the elasticity in direction D1-D2 can be different from an elasticity in direction D3-D4. For example, it is contemplated that the base can be elastic in the D3-D4 direction, but be inelastic in the D1-D2 direction.

As used here, a material having at least a 100% elasticity in a D1-D2 direction is a material that is capable of stretching from its original length to a maximum of twice its original length along D1-D2, and spontaneously resuming its original length. A material having at least a 50% elasticity in a D1-D2 direction is a material that is capable of stretching from its original length to a maximum of 1.5 times its original length along D1-D2, and resuming its original length upon release. In some preferred embodiments, the material could have an at least 25% elasticity in a D1-D2 direction and be capable of stretching from its original length to at least 1.25 times its original length along D1-D2, and resuming its original length upon release. In some preferred embodiments, the material is incorporated into a lower back brace, and has an at least 30% elasticity in a D1-D2 direction and be capable of stretching from its original length to at least 1.3 times its original length along D1-D2, and resuming its original length upon release.

Fasteners 140A and 140B can be coupled to right lateral portion 110C and left lateral portion 110A, respectively, and can be used to releasably fasten the brace around the torso of a wearer.

In some embodiments, hook and loop materials are provided as fasteners 140A and 140B such that the brace can be worn by wearers of various sizes. In some embodiments, multiple snaps, buckles, clasps, clips or other suitable fasteners are provided, and fasteners 140A and 140B (or the materials to which the fasteners are attached) can overlap upon one another and be releasably fastened along several overlapping positions. Viewed from another perspective, the fasteners can allow the brace to serve as a one-size-fits-all or one-size-fits most type of brace, which can be worn by smaller and larger individuals. Additionally or alternatively, the brace can be made to fit users of various sizes via a tightening mechanism provided on one or more portions of the brace, and as described below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the mid-portion 110B can be distinguished from left and right lateral portions 100A and 110C, respectively, as the area having a knitted or cut base portion lacking an inelastic strand running there-through, and including one or more tightening mechanisms. The inelastic strands could comprise, for example, strands 150A, 150B, 150C, 150D, 150E, 150F, 150G, 150H, 150I, 150J, 150K, 150L, which can be threaded, sewn, woven, or otherwise incorporated through the knitted base material during or after knitting, weaving or otherwise manufacturing the elastic base. As illustrated, the mid-portion includes an inelastic tightening mechanism (cord guide housing 155A, cord guide housing 155B, cord 165, and cord 166) which is sized and positioned to overlie the mid-portion. The tightening mechanism can be tightened to (a) shorten the length of the mid-portion when the brace is worn, and (b) effectively make the mid-portion inelastic. In some other embodiments, it is contemplated that one or more portions of the brace can include both inelastic strands and an inelastic tightening mechanism.

With respect to the lateral portions illustrated, the inelastic strands 150A-150L can serve to create zones of inelasticity, wherein the elasticity of a zone in direction D3-D4 is substantially different from an elasticity of the base material alone (without inelastic strands) in direction D3-D4. Viewed from another perspective, the elasticity of the material (base with inelastic strands incorporated there-through) in the D3-D4 direction through which inelastic strands are incorporated can have an effectively reduced elasticity of at least 10%, at least 25%, at least 50% or at least 75% or even more along those zones, relative to the base material alone.

In some aspects, inelastic strands 150A-150L can create zones of inelasticity that are each entirely inelastic in a direction that the inelastic strand is incorporated (e.g., direction D3-D4, direction D1-D2, or any direction in between, for example, between a horizontal and 45 degrees, between a vertical and 45 degrees, or between 25 and 65 degrees relative to the horizontal D3-D4).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

While braces made of non-cut materials, cut materials or both are contemplated, the brace illustrated in FIGS. 1A-1D includes mid and lateral portions that are knit and non-cut. In other words, the mid and lateral portions were knit to have their shapes, and were not cut from an existing piece of material or fabric.

When a brace or brace portion is made of a non-cut material, the inelastic strand(s) included in the lateral portions can be introduced during the knitting, weaving, braiding or other process. Additionally or alternatively, the inelastic strand(s) can be sewn, woven or threaded through the elastic base material after the non-cut material is produced.

In some embodiments, one, two or all of the mid-portion and lateral portions can be made from an elastic base that directly contacts the wearer or the wearer's clothing. One, two or all of the portions can consist of a single layer of material such that the bulkiness of the brace is minimized, and the brace is breathable. For example, the left and right lateral portions can each comprise or essentially consist of a single layer of base material with optional rigid vertical strips (e.g., 115, 125), while the mid-portion could comprise or essentially consist of a first layer of material, a tightening mechanism overlying the layer of material, optional cover materials for the cord guide housings (e.g., 155A and 155B), and an optional rigid vertical strip 120. Viewed from another perspective, it is contemplated that no bulky strapping system or overlying material is required to provide inelasticity.

Viewed from another perspective, it is contemplated that at least 25% of a horizontal midline of the brace could comprise only a single layer of material (excluding inelastic cords 165, 166) when the brace is worn.

Additionally or alternatively, the inner side 100A of mid-portion 110B could comprise inelastic or elastic strips of material 130B and 130A that contact the wearer's body (or wearer's clothing), which can serve as backing materials or sewing stabilizers for cord guide housings 155A and 155B, respectively. Where strips of material 130B and 130A are inelastic, it is contemplated that they can create vertical (or any directional) zones of inelasticity to mid-portion 110B in the D1-D2 direction, the D3-D4 direction, or any other suitable direction. Additionally or alternatively, rigid vertical strips (e.g., 115, 120 and 125) can be included to provide inelasticity or structure to the base material.

It should be appreciated that the inelastic strands, and the optional inelastic or elastic strips of material can be incorporated through or coupled with any suitable portion of a brace, and can have any suitable shape, length and position.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Where a tightening mechanism of a brace comprises inelastic cords 165 and 166 and cord guides, as shown, the inelastic cords 165 and 166 can be configured to wrap at least partially about one or more of the cord guide lobes such that pulling the cords, for example, in opposite directions, shortens the distance between the cord guide housings 155A and 155B. In such embodiments, the pulling of one or more of the cords 165 and 166 can shorten the length of mid-portion 110B via a shortening of the distance between cord guide housings 155A and 155B. In some embodiments, the cords can be pulled in the same direction or any other suitable direction(s). When a desired shortening/tightening is achieved, it is contemplated that the wearer can attach pull tabs 160A and 160B to a portion of the brace via complementary fasteners (e.g., hook or loop of pull tabs, and hook or loop of fasteners 140A and 140B) such that the brace is releasably locked in the desired configuration.

Figure 1C:
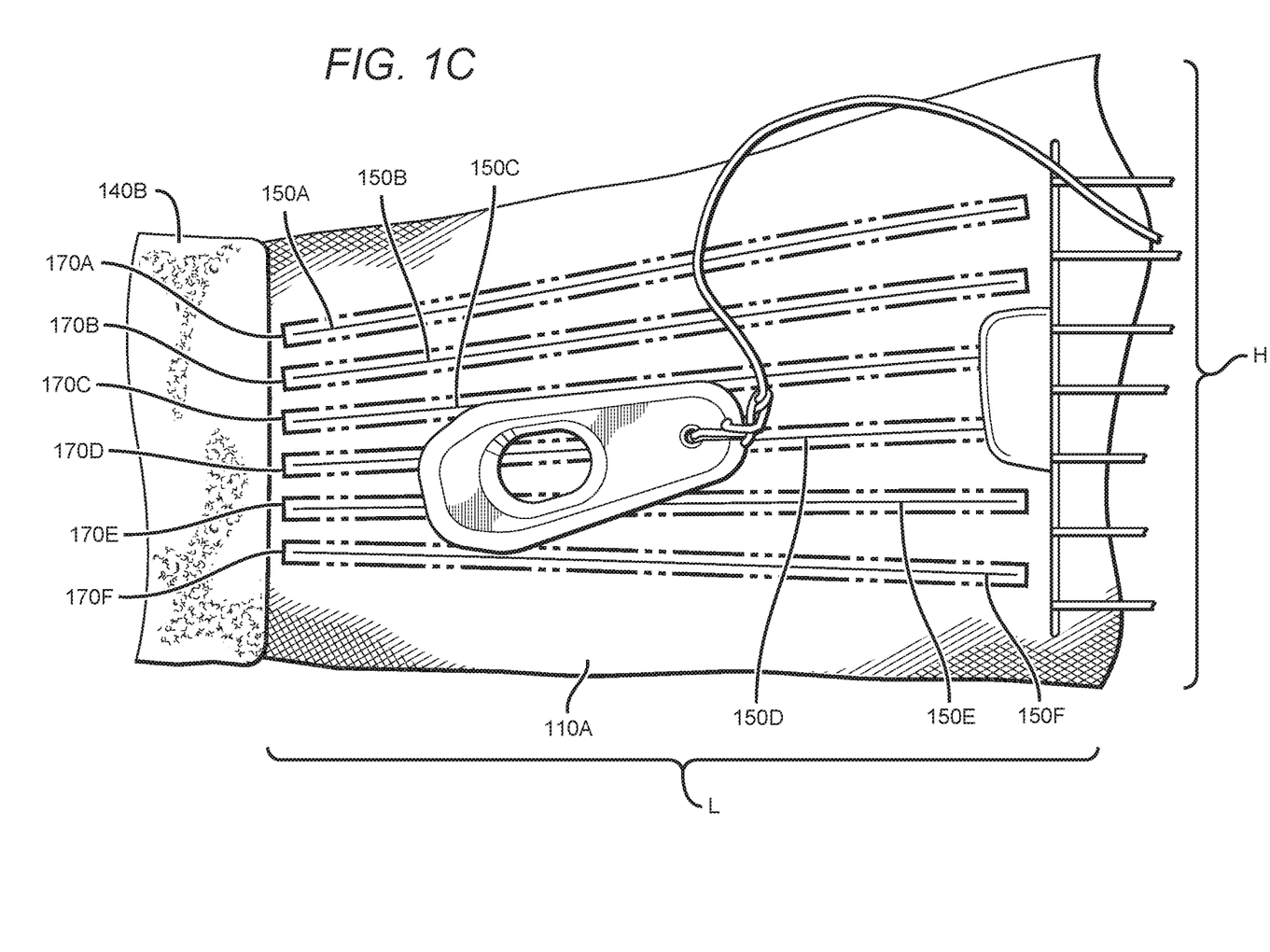
FIG. 1C illustrates an outer surface of a lateral portion of the brace of FIGS. 1A-1B.
Figure 1D:
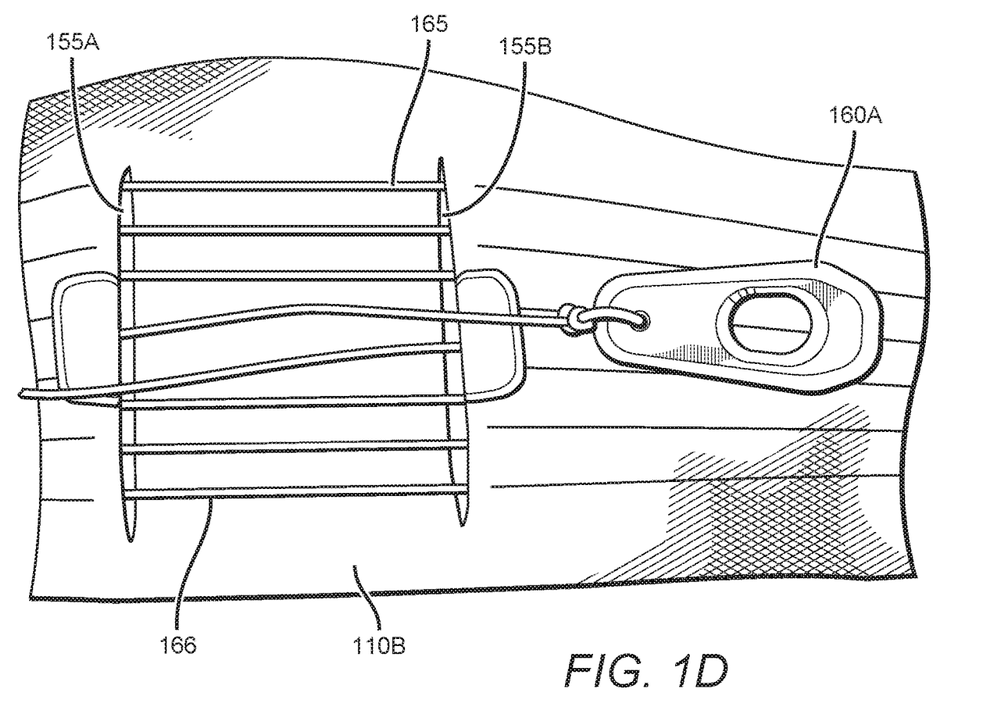
FIG. 1D illustrates an outer surface of the mid-portion of the brace of FIGS. 1A-1C.

FIG. 1C illustrates the left lateral portion 110A of the brace of FIGS. 1A-1B in more detail. As shown, left lateral portion 110A has a length L, and has a height H that is greater near the mid-portion 110B than near fastener 140B. Inelastic strands 150A, 150B, 150C, 150D, 150E and 150F are incorporated through an elastic base material of left lateral portion 110A, which create zones of inelasticity 170A, 170B, 170C, 170D, 170E and 170F, respectively.

In this embodiment, inelastic strand 150A is substantially parallel to 150B (i.e., parallel with one another, or forming an angle of no greater than 25 degrees if an end of strand 150A were touching an end of strand 150B), inelastic strand 150B is substantially parallel to 150C, and so forth. As shown, the inelastic strands are not exactly parallel to neighboring strands. This could be to account for the increase in height H along length L such that a more even distribution of inelastic strands along the length L of the left lateral portion 110A is provided.

Each zone of inelasticity can have any suitable height and length, but will preferably have a height that is no greater than 20%, more preferably no greater than 10%, and even more preferably no greater than 5% of the longest height of the portion it is incorporated in. Additionally or alternatively, where multiple zones of inelasticity are provided on the same portion of a brace, the height of a zone can be less than or equal to 30%, more preferably less than or equal to 20%, and even more preferably less than or equal to 15% of the height or distance between the zones. Additionally or alternatively, the ratio of the surface area of a lateral portion that lacks an inelastic material to the surface area that includes an inelastic material can be at least 25:1, at least 20:1, at least 15:1, at least 10:1, or any other commercially suitable ratio.

Where the zone is not positioned horizontally on the base, the height of a zone is considered the distance between the uppermost and bottommost points of the inelastic strand(s) creating the zone, if the zone was positioned horizontally. As a few examples, the height of a zone can be (1) the same as the thickness of the strand where the strand is incorporated in a straight line (even where the strand is disposed at an angle relative to the horizontal), (2) slightly greater than the thickness of the strand where the strand is incorporated in a slightly curved shape (the height of the curve), (3) the distance between the uppermost point and bottommost point of a zigzagged strand (e.g., H1 or H2 of FIG. 4, even if strands 410 or 420 were incorporated vertically or diagonally), or (4) the distance between the uppermost and bottommost points of two or more inelastic strands that are grouped to create a zone.

A strand can be considered to be a part of a set of strands of a zone when it is spaced apart from a neighboring strand of the zone by no more than 3 times the thickness of the strand.

The strands incorporated into an elastic base can preferably be completely inelastic. However, it is contemplated that some elastic strands can be incorporated, preferably having an elasticity less (e.g., at least 50% less, at least 25% less, at least 75% less, at least 90% less) than an elasticity of the elastic base material (in a direction in which it is incorporated). The elastic or inelastic strands incorporated into the base to define inelastic zones could comprise a string, a plurality of strings (e.g., hemp, cotton, nylon, twine), a wire, a fiber, a rope, a cord, a metal, a plastic, a combination thereof, or any other suitable material(s).

Some preferred strands will have a diameter of no greater than 1 cm (0.3937 inch), and can even have a diameter of between 0.01-5 mm (0.1969 inch), 0.01-3 mm (0.1181 inch), or between 0.01-1 mm (0.03937 inch), 0.01-8 mm (0.315 inch), or 1-9 mm (0.3543 inch). However, thicker strands are also contemplated.

It should be appreciated that brace can include any suitable number of inelastic strands, including between 1-50, between 1-20, between 2-15, between 2-10, or between 3-10, inclusive. It should also be appreciated that brace can include any suitable number of inelastic zones, including between 1-20, between 2-18, between 2-15, between 4-10, or between 4-8, inclusive.

Where thicker or larger zones of inelasticity are desired, it is contemplated that a brace or portion thereof could be made from, for example, strips of material that are elastic or inelastic along their lengths. For example, a brace or portion could comprise top and bottom strips of material that are elastic in a horizontal direction, and a central strip of material disposed between the top and bottom strips and being inelastic or less elastic in the horizontal direction. The height of the central strip of material could be greater than, equal to, or less than a height of the top or bottom strips of material. For example, the central strip and the top strip could have a height-to-height ratio of between 3:1 and 1:3, between 2:1 and 1:2, between 1.5:1 and 1:1.5, between 1:10 and 1:1, between 1:10 and 2:1, between 1:5 and 1:10, or between 1.2:1 and 1:1.2, inclusive.

FIG. 1D illustrates the mid-portion 110B and tightening mechanism of the brace of FIG. 1A-1C in greater detail. Cord guide housings 155A and 155B include cord guides (which can be non-rotating or rotating) that cords 165 and 166 sinuously engage. In the embodiment shown, cord 165 can be pulled in a first direction via pull tab 160A to tighten the top portion of the brace, and cord 166 can be pulled in an opposite direction to tighten the bottom portion of the brace.

Other suitable tightening mechanisms are contemplated, including for example, inelastic pieces of material that extend over the mid-portion 110B and part of one or both lateral portions and fastens thereto, or any cord-based system that can provide a mechanical advantage. With some contemplated tightening systems having separately tensioning components (e.g., multiple cord systems), a user could selectively tighten or loosen different components to target specific muscle groups.

Figure 2A:
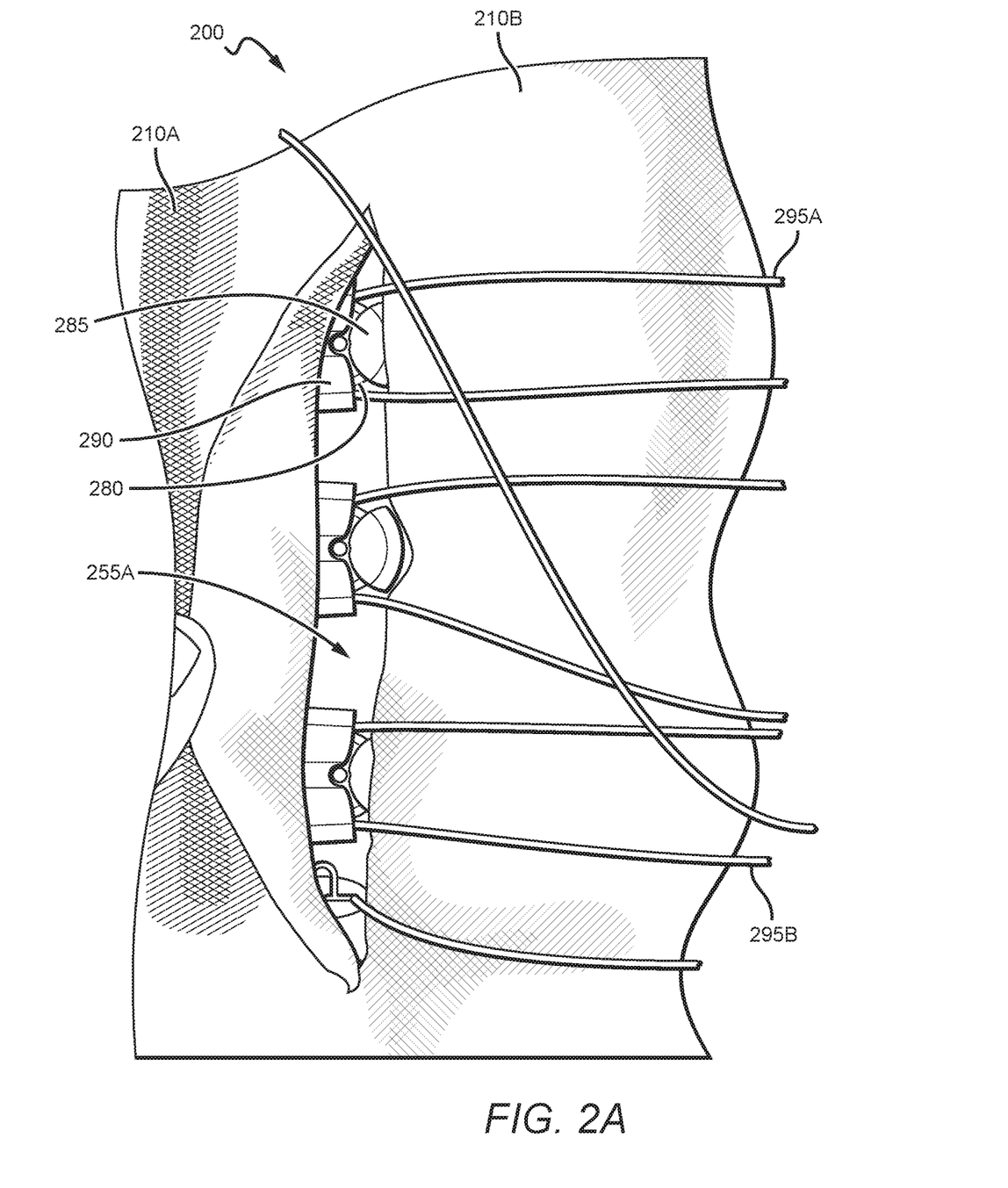
FIG. 2A illustrates an embodiment of a cord guide tightening mechanism shown on an outer surface of a mid-portion of a brace, with a user peeling back the cord guide cover so the cord guide lobes can be seen.
Figure 2B:
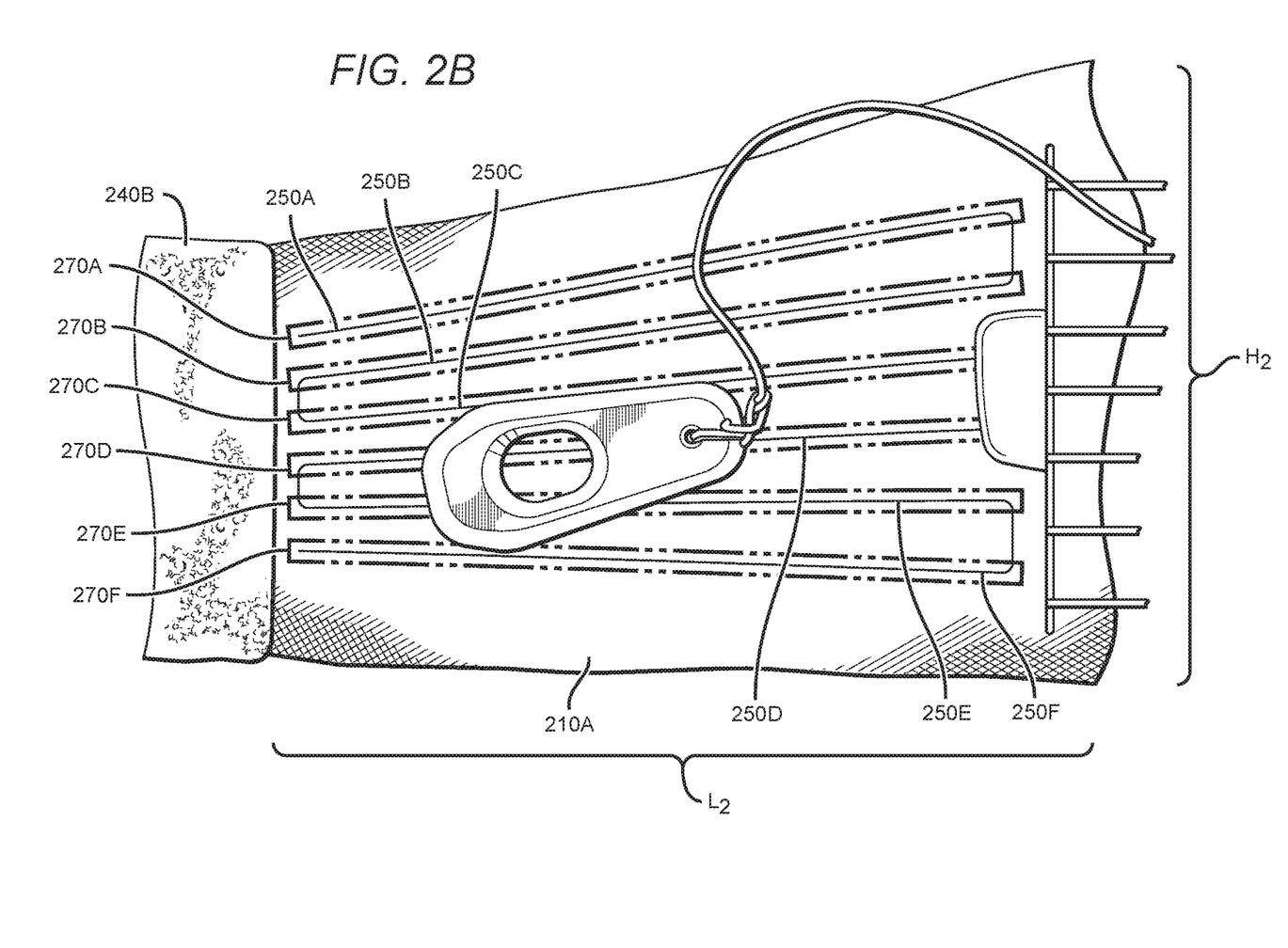
FIG. 2B illustrates a lateral portion of the brace of FIG. 2A wherein the cord guide cover covers the cord guide tightening mechanism.

FIGS. 2A-2B partially illustrate mid portion 210B and left lateral portion 210A of another contemplated brace 200 of the inventive subject matter. Brace 200 includes a tightening mechanism having a first cord guide housing 255A on one end of mid-portion 210B. Although not shown, an identical cord guide housing is disposed on the other side of mid-portion 210B, and rotated 180 degrees. Cord guide housing 255A includes a sheave-housing 290, a sheave-block 285, and a rotating sheave 280 snap fit therein. Sheave 280 is snap fit into sheave-housing 290 through an opening sized and dimensioned to receive sheave 280 and facing left lateral portion 210A. The opening has a central portion that is greater in height, which is sized and dimensioned to allow a centrally disposed pin that extends from each side of sheave 280 to pass through sheave-housing 290 and snap fit between the sheave-housing 290 and sheave-block 285. It is contemplated that in some embodiments the sheave 280 can be removable from sheave-housing 290 (without damaging sheave-housing 290 or any other portion of cord guide housing 255A) through the opening with force. Even in such embodiments, sheave 280 will preferably not be removable in the direction pulled by cord 295A due to sheave-block 285 blocking its movement in that direction.

One or more of the sheaves (e.g., 285) can have a circumferential groove along its thickness, which is sized and dimensioned to receive a thickness of a cord. Here, cords 295A and 295B fit within grooves of each of the sheaves disposed within cord guide housing 255A (and a corresponding cord guide housing not shown), and can be pulled in opposite directions to shorten the distance between the cord guide housings and tighten the brace. Again, sheave-blocks (e.g., 285) can act to help keep sheaves (e.g., 280) in place when a cord (e.g., 295A) is pulled in the direction of the sheave-block (e.g., 285) relative to the sheave-housing (e.g., 290).

Left lateral portion 210A is similar to the left lateral portion shown in FIG. 1C except that each of the zones of inelasticity 270A, 270B, 270C, 270D, 270E, and 270F are all defined by a single inelastic strand (or single set of inelastic strands) that is incorporated into an elastic base. The single inelastic strand includes "substantially horizontally" oriented strand portions 250A, 250B, 250C, 250D, 250E, and 250F (within 25 degrees of horizontal), and "substantially vertically" oriented portions (within 25 degrees of horizontal) extending there-between.

Although a single strand or single set of strands is used, different zones of inelasticity 270A, 270B, 270C, 270D, 270E, and 270F are created since the substantially horizontally oriented strand portions 250A, 250B, 250C, 250D, 250E, and 250F are separated by a distance that is greater than 3 times the thickness of the strand or set of strands.

Where the left lateral portion includes a base material that is vertically elastic, it should be appreciated that an elasticity in the vertical direction can be reduced (e.g., by between 1-50%, by between 5-25%, by between 5-15%, by 100%) at certain positions along length L2 where the inelastic strand extends vertically. Alternatively or additionally, the single strand could be incorporated in one shape in the substantially horizontal direction (e.g., straight, slightly curved), and in another shape in the substantially vertical direction (e.g., zigzagged). This would allow the brace to maintain more of the base material's elasticity in the vertical direction.

Figure 3:
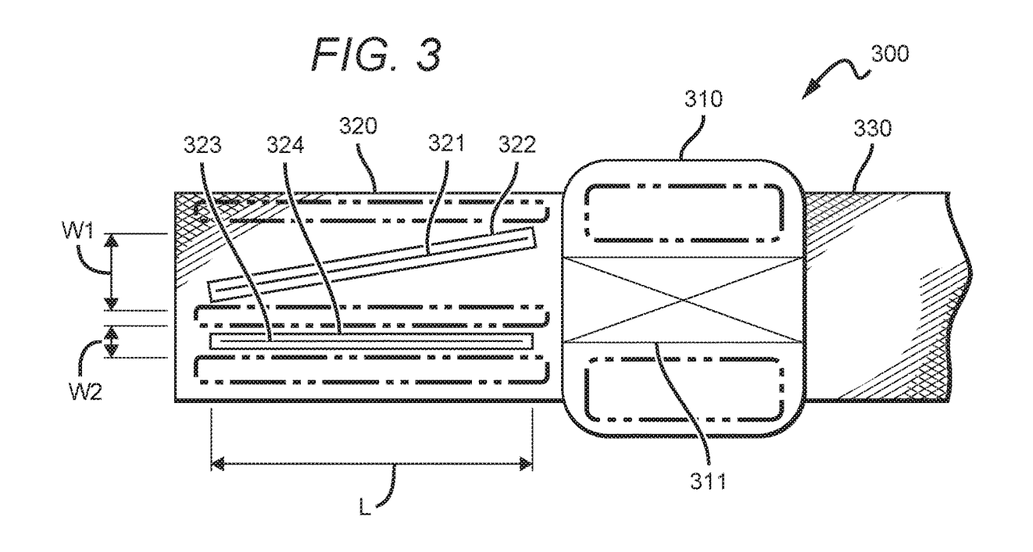
FIG. 3 illustrates another embodiment of a brace of the inventive subject matter showing elastic and inelastic zones in dotted lines.

FIG. 3 illustrates yet another brace 300 of the inventive subject matter having mid portion 310 and lateral portions 320 and 330. Mid-portion 310 and lateral portion 320 each comprise a knit or cut elastic base material having an elasticity in a horizontal direction that is the same as an elasticity in a vertical direction. Mid-portion 310 includes a tightening mechanism 311 that can cause mid-portion 310 (or portions thereof) to be made effectively inelastic in some areas upon tightening. As shown, several areas of the mid-portion 310 will remain effectively elastic even when tightening mechanism 311 is tightened and the brace is worn. These areas include, for example, the areas shown within the dotted box boundaries.

Lateral portion 320's elastic base material has a plurality of strands 321 and 323 incorporated there-through across Length L, which define zones of inelasticity 322 and 324, respectively. Strand 321 forms an angle with the bottom edge of lateral portion 320, and thus defines a zone of inelasticity 322 that has a greater extent W1 than the extent W2 of zone 324, which is defined by substantially horizontal strand 323. The remaining areas shown within the dotted lines lack inelastic strands and thus can maintain their elasticity.

As used herein, the "extent" is the portion of the height of the base along which an inelastic strand extends. The extent of a zone can in some embodiments be the same as the height of the zone, for example, where the strand is disposed horizontally.

Figure 4:
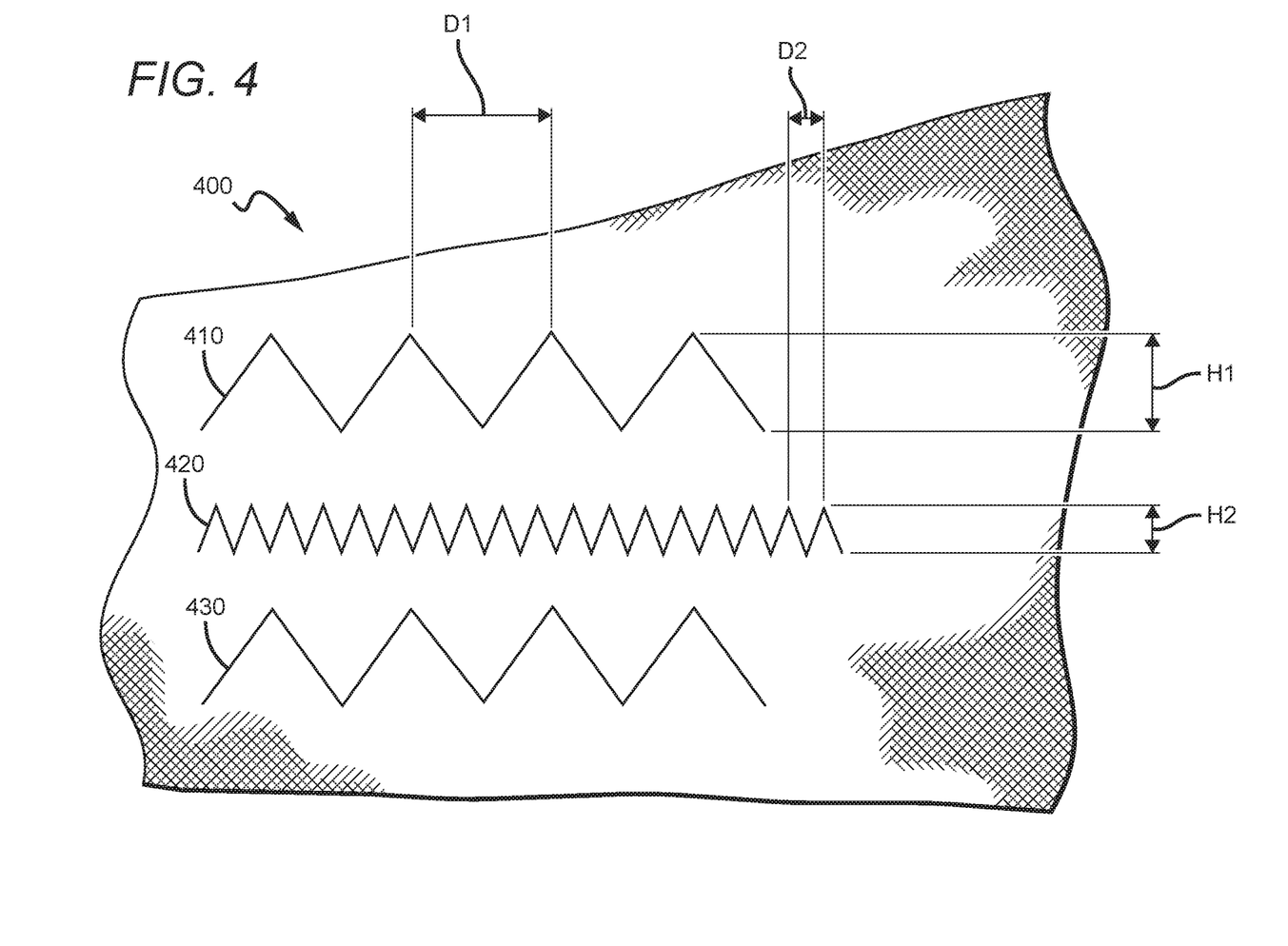
FIG. 4 illustrates a brace portion having inelastic strands incorporated in zigzagged patterns.

FIG. 4 illustrates an exemplary brace portion 400 having gradated or otherwise non-uniform zones of inelasticity. These non-uniform zones could be provided, for example, by inelastic strands incorporated into an elastic base to have different shapes or sizes, or via elastic strands having less elasticity than the elastic base in at least one direction.

In FIG. 4, first inelastic strand 410 is incorporated having a peak to peak distance of D1, and a vertical height of H1. A second inelastic strand 420 is incorporated having a peak to peak distance of D2 and a vertical height of H2. A third inelastic strand 430 is incorporated beneath strand 420 and has the same peak to peak distance D1 and vertical height H1 as strand 410. The zones of inelasticity created by strands 410 and 430 could be more or less elastic than the zone of inelasticity created by strand 420.

If, for example, the materials of the strands were the same, and the height (H1 and H2), and length of zones were the same, the first inelastic strand 410 could create a zone of inelasticity that has a greater inelasticity than the second zone created by the second inelastic strand 420 (e.g., at least 10% less elastic, at least 20% less elastic, at least 50% less elastic, or even at least 75% less elastic) if the distance D1 between peaks is greater than the distance D2.

While the inelastic strands shown in FIG. 4 comprise uniform V-shaped zigzags, it is contemplated that a strand having any zigzag pattern could be incorporated into the elastic base material. For example, an inelastic strand could be incorporated having various shapes (e.g., v-shaped, s-shaped, flat) throughout its length. Where the inelastic strand includes a flat or wide peak or valley, the distance between two peaks can be calculated as the distance from the midline of one peak to the midline of another peak.

Where a gradated set of inelastic zones are provided, it is contemplated that the first zone created by a first inelastic strand could be more inelastic than the second zone created by a second inelastic strand, and the second zone could be more inelastic than the third zone created by the third inelastic strand (e.g., at least 10% less elastic, at least 20% less elastic, at least 50% less elastic, or even at least 75% less elastic). Viewed from another perspective, the material comprising the elastic base and inelastic strands can have an elasticity in the first direction along the first zone of inelasticity that is at least 20% less, at least 50% less or even at least 75% less than an elasticity in the first direction along the second zone of inelasticity.

As another example, a first inelastic strand could be incorporated in a substantially straight line across a portion of a brace's base material. A second inelastic strand could be incorporated below the first inelastic strand in a zigzagged shape having a first distance between a first peak and a second peak. Additionally, a third inelastic strand could be incorporated below the second inelastic strands in a zig-zagged shape having a second distance between a first peak and a second peak, the first distance being larger than the second distance.

It should be appreciated that the inelasticities of the zones created by strands incorporated to have different shapes does not need to be gradated. Indeed the first, second, third, and any additional strands, can be incorporated in any order along any suitable portion of the brace.

Figure 5A:
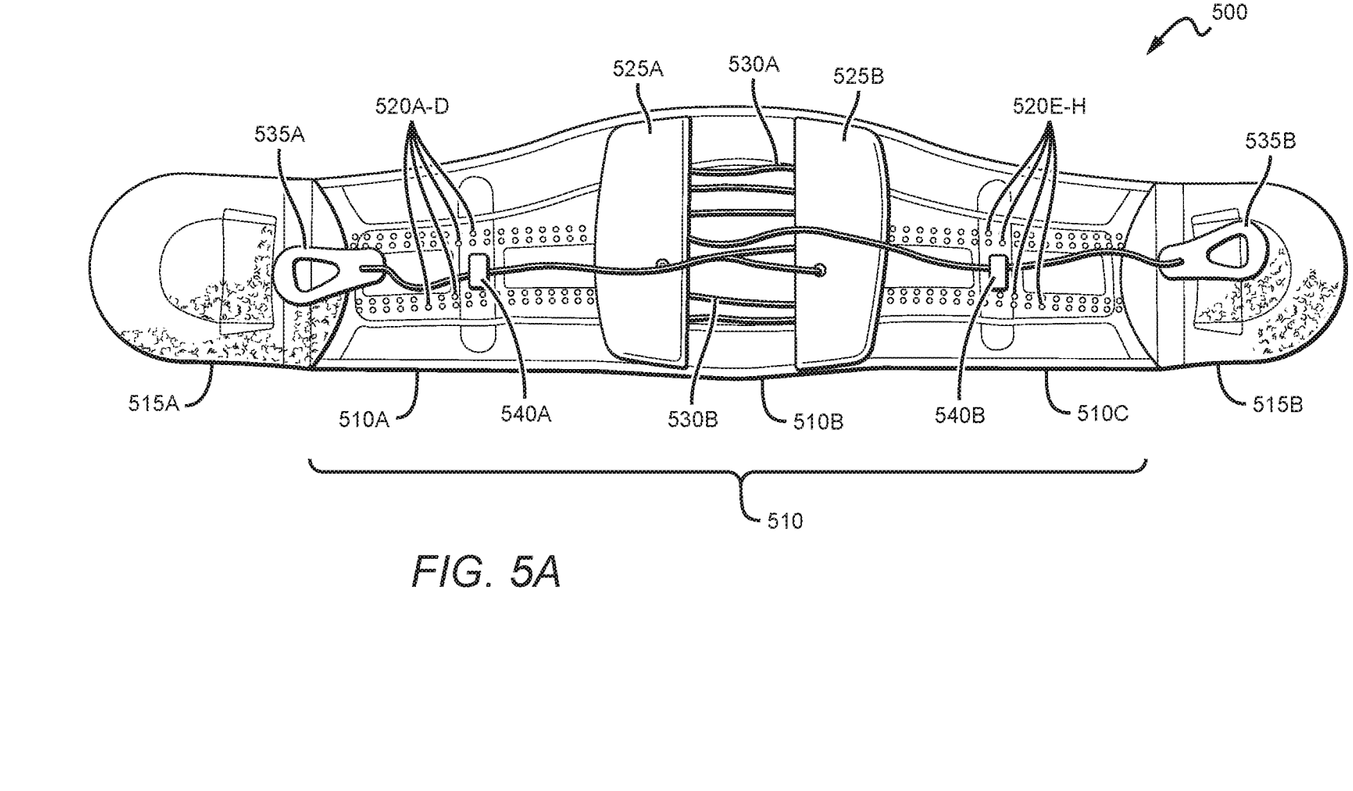
FIG. 5A illustrates an outer surface of another brace of the inventive subject matter.
Figure 5B:
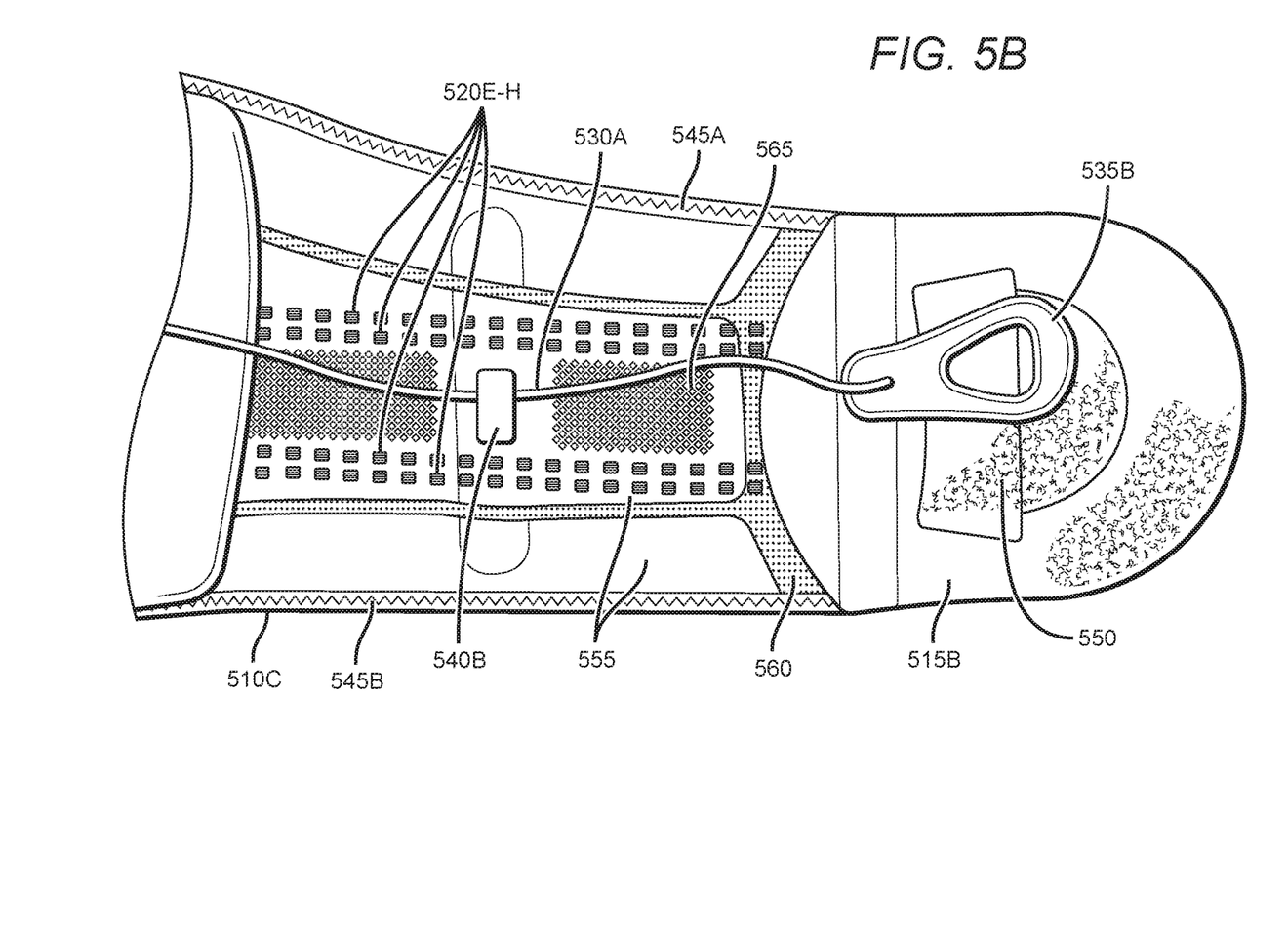
FIG. 5B illustrates a portion of the brace of FIG. 5A.

FIGS. 5A-5B illustrate another brace 500 of the inventive subject matter having an elastic base, and eight zones of inelasticity defined by eight pairs of inelastic strands that are thread through the elastic base. Brace 500 is configured to wrap around the trunk of wearers of different sizes and shapes, and fasten upon itself via hook and loop fasteners 515A and 515B. When brace 500 is worn, it is configured to provide an inelastic section along the mid-horizontal length of the brace via the eight inelastic zones, and the tightening system. The top and bottom edges maintain a greater elasticity, and can conform to the wearer's curvatures.

Brace 500 comprises an elastic base 510, which is coupled to a first fastener 515A on a first end and a second fastener 515B on a second end. The elastic base 510 comprises three pieces or portions, including first base portion 510A, second base portion 510C, and third portion 510B positioned therebetween. In some contemplated embodiment, the elastic base 510 could comprise fewer or more panel pieces or portions (e.g., 1, 2, 4, 5, 6). The first base portion 510A and sets of inelastic strands 520A-D make up a first lateral portion of brace 500, the second base portion 510C and sets of inelastic strands 520E-H make up a second lateral portion of brace 500, and third base portion 510B and a tightening system make up the mid-portion of brace 500. It is contemplated that each portion of the brace can comprise one or more knitting or weaving patterns, which can affect to what extent the brace can be stretched. For example, second base portion 510C includes a first knit pattern 555, which is visually distinct from second knit pattern 560, which is different from third knit pattern 565. Third knit pattern 565 is positioned between inelastic zones defined by 520E-F and inelastic zones defined by 520G-H, and comprises an open mesh pattern that allows for greater airflow. It should be appreciated that any suitable combination of knit patterns could be provided.

Elastic base 510 can be elastic in a horizontal direction, and can optionally be elastic in the vertical direction. Third base portion 510B can include or be coupled to a tightening system that includes inelastic or elastic cord guide covers 525A and 525B that cover cord guide housings similar to those illustrated and described in FIGS. 2A-2B (e.g., 255A). Because the third base portion 510B lacks any inelastic strands that define inelastic zones, the user is able to stretch the belt around its mid-portion, and fasten upon itself via hook and loop fasteners 515A and 515B to obtain a desired fit. The user could then further tighten the brace using the tightening system. It should be appreciated that brace 500 could be worn with cord 530A positioned above cord 530B, and with the curvier edge being positioned above the flatter edge. It should also be appreciated that brace 500 could be worn with cord 530B positioned above cord 530A, and with the curvier edge being positioned below the flatter edge.

First and second cords 530A and 530B are inelastic, and extend across the third portion 510B between the cord guide housings. When the brace is worn, pull tab 535B can be pulled in a first direction to pull cord 530A, tighten an upper portion of brace 500 (or lower portion depending on how the brace is worn), and shorten a distance between cord guide housing covers 525A and 525B. Pull tab 535A can be pulled in the same or different direction to pull cord 530B, tighten a lower portion of brace 500 (or upper), and shorten a second distance between cord guide housing covers 525A and 525B.

Sets of inelastic strands 520A-D on first base portion 510A can extend between cord guide housing covers 525A and fastener 515A to define four zones of inelasticity. Sets (e.g., pairs) of inelastic strands 520A-D could extend across between 0-100%, between 25-100%, between 25-75%, between 50-100%, between 75-100%, between 80-100%, or between 90-100% of the length between cord guide housing cover 525A and fastener 515A. Sets of inelastic strands 520E-H on second base portion 510C can extend between cord guide housing cover 525B and fastener 515B to define four additional zones of inelasticity. Sets of inelastic strands 520E-H could extend across between 0-100%, between 25-100%, between 25-75%, between 50-100%, between 75-100%, between 80-100%, or between 90-100% of the length between cord guide housing cover 525B and fastener 515B.

In some contemplated embodiments, cord guide housing covers 525A and 525B, and fasteners 515A and 515B are inelastic in the horizontal direction, sets of inelastic strands 520A-D extend across 85-100% of the length between cord guide housing cover 525A and fastener 515A, and sets of inelastic strands 520E-H extend across 85-100% of the length between cord guide housing cover 525B and fastener 515B. When brace 500 is worn and pull tabs 535A and 535B have been pulled and removably fastened to fasteners 515A, 515B, or any other portion of the brace, the top and bottom edges of the brace can have an elasticity sufficient to conform to the curves of the wearer without pinching, and a portion between the top and bottom edges can be less elastic, or even inelastic due to the sets of inelastic strands 520A-H, and cords 530A and 530B. The first base portion 510A can include a cord loop 540A through which cord 530B can pass through and be held in place. The second base portion 510C can include a second cord loop 540B through which cord 530A can pass through and be held in place between sets of inelastic strands 520E-F, and sets of inelastic strands 520G-H. Fasteners 515A and 515B can each include a larger loop (e.g., loop 550) that is configured to receive a pull tab or the wearer's hand when the brace is being put on.

In some contemplated embodiments, a lower back brace is provided comprising a belt having a mid-panel or portion positioned between first and second lateral panels or portions. The belt could be made as a single piece, or could be made as two or more separate panels that are directly or indirectly coupled to one another. Each of the panels or portions could comprise an elastic base that is elastic in one or more directions. In some embodiments, the elastic base will be elastic in a horizontal direction, but be inelastic in a vertical direction. In some embodiments, the elastic base will be elastic in both horizontal and vertical directions. In such embodiments, the elasticities in horizontal and vertical directions could be the same or different. For example, the elastic base could be configured to stretch up to 110%, 120%, 125%, 130%, 140%, 150%, 200% or even more of its original length in the horizontal direction, and return to its original length. Additionally or alternatively, the elastic base could be configured to stretch up to 110%, 120%, 125%, 130%, 140%, 150%, 200% or even more of its original length in the vertical direction, and return to its original length. Additionally or alternatively, the elastic base could be configured to stretch up to 110%, 120%, 125%, 130%, 140%, 150%, 200% or even more of its original length in a horizontal or other direction, and return to its original length.

One or more sets of inelastic strands can be incorporated into one or more of the panel or portion's elastic bases to define inelastic or compression zones between two non-compression or elastic zones. A panel or portion that includes a compression or inelastic zone could have an elasticity (zone elasticity) along, and in the direction of the compression or inelastic zone, that is at least 50% less, at least 75% less, or even 100% less (i.e., inelastic, 0% elasticity) relative to the elasticity of the elastic base alone in the same direction.

The inelastic strands can be incorporated generally in a direction that the brace is elastic, although the strands can be curved, straight (e.g., horizontally aligned), or zigzagged. The set of inelastic strands for a zone (e.g., 1, 2, 3, 4, 5 or even more strands) can be incorporated into the elastic base of the belt panel or portion such that it extends across at least 25%, at least 50%, at least 75% or even between 80-100% of a length of the elastic base. For example, the set of inelastic strands could be incorporated into the elastic base of a lateral panel such that it extends across between 90-100% of a horizontal length of the lateral panel.

Each inelastic zone can have a height that is less than 20%, more preferably less than 10% or even less than 5% of the height of the panel or portion the inelastic strands defining the zone are incorporated into. Each inelastic zone can have a length that is at least 10%, at least 20%, at least 50%, at least 75% or even 90-100% of the length of the panel or portion the inelastic strand defining the zone are incorporated into. For example, an inelastic zone could have a length that is at least 5 inches (12.7 cm), and a height of less than 1 inch (2.54 cm). As another example, an inelastic zone could have a length that is at least 8 inches (20.32 cm), and a height of less than 0.5 inch (1.27 cm).

Each inelastic zone can have an extent that is less than 50%, less than 40%, less than 30%, less than 20%, less than 10% or even less than 5% of the height of the panel or portion the inelastic strands defining the zone are incorporated into. Contemplated braces, panels and portions can include any suitable number of inelastic zones between elastic zones.

For example, Brace 500 includes 8 inelastic zones, 4 inelastic zones on each of the first and second lateral panel portions. Each inelastic zone is positioned between two elastic zones, and each inelastic zone is defined by a pair of inelastic strands. Each zone can be separated from another zone by any suitable distance, including for example, at least 0.5 inch (1.27 cm), at least 1 inch (2.54 cm), at least 2 inches (5.08 cm), between 1-3 inches (2.54-7.62 cm), between 1-5 inches (2.54-12.7 cm), between 2-4 inches (5.08-10.16 cm), or between 2-6 inches (5.08-15.24 cm). The inelastic zones of brace 500 are separated by different distances. For example, the inelastic zone defined by the set of strands 520B is separated from the inelastic zone defined by set of strands 520A by less than 1 inch (2.54 cm), but is separated from the inelastic zone defined by set of strands 520C by more than 2 inches (5.08 cm).

Preferably, the belt's top and bottom edges will each have a horizontal elasticity that is greater than the elasticity of the zone elasticity described above. Additionally, the belt's top and bottom edges will each preferably have an elasticity that is greater than the elasticity of the horizontal section of the belt that includes any inelastic zone. For example, at least one of the top and bottom edges can have the same elasticity as the elastic base.

In some embodiments, a brace provides support to a lower spine of a wearer, and comprises: a belt having a first end and a second end; wherein the first end is coupled to a first fastener, and the second end is coupled to a second fastener; and wherein the belt has a first belt elasticity in a first direction that is unequal to a second belt elasticity in a second direction orthogonal to the first direction, and comprises: (a) an elastic base having a first base elasticity in the first direction that is substantially the same as a second base elasticity in the second direction; and (b) a first set of inelastic strands incorporated into the elastic base along a first length in the first direction to define a first inelastic zone.

In some embodiments, a brace provides support to a lower spine of a wearer, and comprises: a belt having a mid portion positioned between a first lateral portion and a second lateral portion; wherein the first lateral portion comprises: (a) a base having a first base elasticity in a first direction; (b) a first set of inelastic strands incorporated into the base in the first direction and along a first portion of the base to define a first inelastic zone having a height of less than 1 inch (2.54 cm), and a length of at least 5 inches (12.7 cm); and (c) wherein the first portion of the first lateral portion has a first combined elasticity in the first direction that is at least 50% less than the first base elasticity.

In some embodiments, a material is provided comprising: an elastic base having a first base elasticity in a first direction; a first set of inelastic strands incorporated into the elastic base in the first direction and along a first portion of the elastic base to define a first zone of inelasticity; wherein the first zone of inelasticity has a height no greater than 10% of a height of the elastic base; wherein a first strand of the first set of inelastic strands has a thickness of less than 3 mm (0.1181 inch); and wherein the material has a first combined elasticity in the first direction and along the first portion that is at least 25% less than the first base elasticity.

In some embodiments, a brace provides support to a lower spine of a wearer, and comprises: a belt having a mid portion disposed between a first lateral portion and a second lateral portion; and wherein at least one of the mid portion, the first lateral portion and the second lateral portion comprises: (a) a first elastic base having a first base elasticity in the first direction and a second base elasticity in the second, substantially orthogonal direction; (b) a first inelastic strand incorporated into the first elastic base along a first length to define a first inelastic zone along the first direction; and (c) wherein the first inelastic zone has an elasticity that is at least 50% less than the first base elasticity.

In some embodiments, a brace provides support to a lower spine of a wearer, and comprises: a belt having a mid portion disposed between a first lateral portion and a second lateral portion; and wherein at least one of the mid portion, the first lateral portion and the second lateral portion comprises: (a) a first inelastic portion disposed substantially horizontally and directly between first and second elastic portions, wherein each of the first inelastic portion and the first and second elastic portions have the same length when the brace is in a resting configuration; and (b) wherein the first inelastic material portion has a shorter length than the first elastic material portion when the brace is in a stretched configuration.

Thus, various braces and materials for braces providing benefits of both inelastic and elastic materials have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A panel for a brace that provides support to a lower spine of a wearer, comprising:
    an elastic base having a first elasticity in a longitudinal direction;
    a first inelastic strand incorporated into the elastic base along the longitudinal direction configured to define a first inelastic zone, and a first elastic zone and a second elastic zone bordering opposite sides of the first inelastic zone, respectively; and
    wherein the panel has a second elasticity in a transverse direction at least 50% of the first elasticity.

2. The panel of claim 1, wherein the brace comprises a belt, and the panel is configured to attach to a second panel through a mid-panel.

3. The panel of claim 2, wherein the mid panel has a cord guide.

4. The panel of claim 1, further comprising a second inelastic strand substantially parallel to the first inelastic strand.

5. The panel of claim 4, wherein a medial end the first inelastic strandis separated by at least two inches from a medial end of the second inelastic strand.

6. The panel of claim 1, wherein the elastic base is knitted.

7. The panel of claim 6, wherein the elastic base comprises at least two distinct knit patterns.

* * * * *

UNITED STATES PATENT AND TRADEMARK OFFICE
CERTIFICATE OF CORRECTION

PATENT NO. : 11,273,068 B2
APPLICATION NO. : 16/406367
DATED : March 15, 2022
INVENTOR(S) : Steven Burke, Jozsef Horvath and Erik Zimmer It is certified that error appears in the above-identified patent and that said Letters Patent is hereby corrected as shown below:

In the Claims

Column 20, Line 12, Claim 5 change, "inelastic strandis separated by" to --inelastic strand is separated by--

Signed and Sealed this
Fifteenth Day of November, 2022

Katherine Kelly Vidal
Director of the United States Patent and Trademark Office